United States Patent
Godek et al.

(10) Patent No.: US 9,700,563 B2
(45) Date of Patent: Jul. 11, 2017

(54) KAPPA OPIOID RECEPTOR COMPOUNDS

(71) Applicants: Dennis Michael Godek, Glastonbury, CT (US); Harry Ralph Howard, Bristol, CT (US)

(72) Inventors: Dennis Michael Godek, Glastonbury, CT (US); Harry Ralph Howard, Bristol, CT (US)

(73) Assignee: MediSynergies, LLC, Farmington, CT (US)

( * ) Notice: Subject to any disclaimer, the term of this patent is extended or adjusted under 35 U.S.C. 154(b) by 0 days.

(21) Appl. No.: 15/135,433

(22) Filed: Apr. 21, 2016

(65) Prior Publication Data
US 2016/0235759 A1    Aug. 18, 2016

Related U.S. Application Data

(63) Continuation of application No. 13/958,579, filed on Aug. 4, 2013, now Pat. No. 9,346,777.

(60) Provisional application No. 61/697,799, filed on Sep. 6, 2012.

(51) Int. Cl.
| | |
|---|---|
| *A61K 31/5377* | (2006.01) |
| *A61K 31/4025* | (2006.01) |
| *A61K 31/4178* | (2006.01) |
| *A61K 31/343* | (2006.01) |
| *C07D 405/06* | (2006.01) |
| *C07D 405/04* | (2006.01) |
| *C07D 307/87* | (2006.01) |

(52) U.S. Cl.
CPC ........ *A61K 31/5377* (2013.01); *A61K 31/343* (2013.01); *A61K 31/4025* (2013.01); *A61K 31/4178* (2013.01); *C07D 307/87* (2013.01); *C07D 405/04* (2013.01); *C07D 405/06* (2013.01)

(58) Field of Classification Search
CPC combination set(s) only.
See application file for complete search history.

(56) References Cited

U.S. PATENT DOCUMENTS 6,921,774 B2 *  7/2005  Moltzen ................ C07C 229/14
                                                        514/443
9,346,777 B2 *  5/2016  Godek .................. C07D 307/87

OTHER PUBLICATIONS

Mehr-un-Nisa et al. "Synthesis of novel triazoles and a tetrazole of escitalopram as cholinesterase inhibitors" Bioorg. Med. Chem. 2015, 23, 6014-6024.*
Black D, Trevethick M "The Kappa opioid receptor is associated with the perception of visceral pain", Gut, 1998, 43:312-313.
Feng YL, Roth B "Salvinorin A: A novel and highly selective K-opioid receptor agonist ", Life Sciences, 2004, 75:2615-2619.
Riviere PJ-M "Peripheral kappa-opioid agonists for visceral pain" British Journal of Pharmacology, 2004, 141:1331-1334.
Simonin F, Valverde O, Smadja C, et al "Disruption of the K-opioid receptor gene in mice . . . " EMBO Journal, 1998, 17(4): 886-897.
Treede R-D, Rief W, Barke A, et al "A Classification of Chronic Pain for ICD-11", Pain, 2015, 156(6): 1003-1007.
Zhou L, Lovell KM, Frankowski KJ, et al "Development of Functionally Selective, Small Molecule Agonists at Kappa Opioid Receptors" J. Biol. Chem. 2013, 288(512): 36703-36716.

* cited by examiner

*Primary Examiner* — Michael Barker
*Assistant Examiner* — Amanda L Aguirre

(57) ABSTRACT

The invention is directed to a method of treatment for chronic pain, the method comprising administering to a mammal in need of such treatment a therapeutically effective amount of a compound of formula I, or a pharmaceutically acceptable salt thereof.

12 Claims, No Drawings

KAPPA OPIOID RECEPTOR COMPOUNDS

This application claims the benefits of U.S. Provisional Application No. 61/697,799 filed Sep. 6, 2012.

BACKGROUND OF THE INVENTION

This invention is directed to a method of use for the treatment of pain in a mammal comprising the administration of a therapeutically effective amount of a compound of formula I, or a pharmaceutically acceptable salt thereof, and a pharmaceutically acceptable carrier.

Clinically, pain is associated with a variety of diseases and disorders including cancer, traumatic nerve damage, diabetic neuropathy and spinal cord injury, which are generally perceived by patients to be chronic and debilitating. The International Association for the Study of Pain (IASP) recently organized a task force of pain experts to define chronic pain for the World Health Organization's latest issue of *International Classification of Diseases* (*ICD*) (see R-D Treede et al, "A classification of chronic pain for ICD-11" (2015) Pain, 156(6):1003-1007). The major categories in the new classification include chronic pain from cancer, post-traumatic nerve damage, diabetic neuropathy, chronic primary pain, fibromyalgia, post-surgical pain, chronic visceral pain and musculoskeletal pain.

Whereas moderate pain is often treated with analgesics (for neuropathic pain) or anti-inflammatory drugs (for inflammation induced pain, e.g. in arthritis), morphine and related opiate analgesics are the most effective and, therefore, the most widely prescribed drugs for the treatment of chronic, severe pain. However, opiates are frequently over-prescribed and potentially dangerous when misused or abused by patients, leading to dependency. They may also be associated with side effects including dysphoria, sedation, gastrointestinal disturbances and death.

Opioid receptors are found in the Central Nervous System (CNS) of mammals, especially humans, and are included in the broader class of G-Protein Coupled Receptors (GPCRs). They have been further characterized, based on their functional reactivity to specific agonists and antagonists, as delta (δ), kappa (κ) and mu (μ) subtypes. These DOR (delta), KOR (kappa) and MOR (mu) opioid receptors, respectively, are highly distributed in the CNS in areas associated with pain, including the cerebral cortex, amygdala, hypothalamus and spinal cord.

KORs are also expressed in the peripheral nervous system, and activation of these receptors by selective agonists has been shown to produce a reduction of pain and inflammation in animal studies designed to model human pain (T W Vanderah, (2010) Clinical Journal of Pain, 26:S10-S15) (F. Simonin et al, (1998) EMBO Journal, 17:886-897) (D Black and M Trevethick, (1998) Gut 43:312-313) (L Zhou et al (2013) Journal of Biological Chemistry 288: 36703-36716) (P J Riviere, (2004) British Journal of Pharmacology 141:1331-1334)

However, activation of central KORs may also be associated with significant dysphoria, which can promote addiction in patients, as well as heightened anxiety and restless behavior. It is predicted that selective KOR agonists that do not cross the blood-brain barrier could provide a significant advantage in the treatment of severe pain without the associated CNS side effects observed with some potent opiate analgesics currently in use. KOR activation by specific agonists such as the highly selective KOR agonist Salvinorin A, have produced "spaciotemporal dislocation rather than hallucinatory behavior that is frequently dysphoric" (Feng Y and Roth B L (2004) Life Sciences 75:2615-2619)

Cara Therapeutics, a biotech company in Shelton, CT recently announced their collaboration with the Japanese firm Maruishi to develop and commercialize CR845, a peripherally-restricted kappa opioid receptor agonist for the treatment of acute and chronic pain (http://prnewswire.com/new-releases/cara-therapeutics-enters-into-development-and-commercial-alliance-with-maruishi-for-novel-kappa-opioid-agonist-cr845-in-japan-205205391.html). CR845 is a peptide-based KOR agonist that has not displayed dysphoric behavior or hallucinations in Phase II trials in the U.S., reportedly it shows a reduced incidence of nausea and vomiting in post-operative patients. Nektar Therapeutics of San Francisco, Calif. has also presented pre-clinical data for their oral, peripherally acting KOR agonist NKTR-195 (http://ir.nektar.com/releasedetail.cfm?ReleaseID=871723).

The present application discloses a new series of compounds with potent and selective KOR agonist activity which may offer an effective, better tolerated treatment for chronic pain.

SUMMARY OF THE INVENTION

This invention is directed to the use of a therapeutically effective amount of a compound of the formula I:

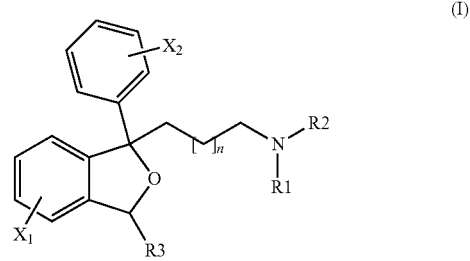

or a pharmaceutically acceptable salt thereof, in the treatment of pain in a mammal, wherein:

$X_1$ is a group of the general formula:

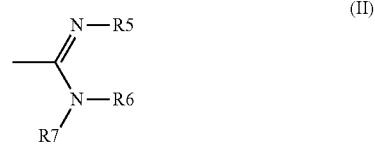

or $X_1$ is a heteroaryl ring, selected from the list comprising 2-imidazolyl, 4-imidazolyl, 2-thiazolyl, 4-thiazolyl, 5-thiazolyl, 2-oxazolyl, 4-oxazolyl, 5-oxazolyl, 1,2,4-thiadiazol-3-yl, 1,2,4-thiadiazol-2-yl, 1,2,4-thiadiazol-4-yl, 1,2,3-triazolyl-2-yl, 1,2,3-triazol-1-yl, 1,2,4-triazol-1-yl, 1,2,4-triazol-3-yl, 1,2,4-triazol-4-yl, 1,3-thiazol-2-yl, 1,3-thiazol-4-yl, 1,2,3,4-tetrazol-5-yl, 1,2,3,4-tetrazol-1-yl, 1,2,4-oxadiazol-3-yl, 1,2,4-oxadiazol-2-yl, 1,2,4-oxadiazol-3-yl, 1,2,4-oxadiazol-5-yl, 1,3-pyrimidin-2-yl, 1,2-pyrazin-3-yl and 1,2,4-triazin-3-yl;

R5 and R6, taken together with the N—C═N group to which they are attached form a 5- to 10-membered cyclic or bicyclic ring, optionally substituted with up to two additional heteroatoms selected from the group consisting of N, O or S; or R6 and R7, taken together with the nitrogen atom to which they are attached form a 5- to 10-membered cyclic or bicyclic ring, optionally substituted with up to two additional heteroatoms selected from the group consisting of N, O or S; or R5, R6 and R7 are independently defined as H, $C_1$-$C_6$ alkyl, $C_3$-$C_7$-cycloalkyl, aryl, or heteroaryl;

$X_2$ is H, Br, Cl or F;

R1 and R2 are independently hydrogen or methyl;

R3 is hydrogen; and n is zero, one or two.

The invention is also directed to a pharmaceutical composition for treating pain in a mammal, including a human, by administering a pharmacologically effective amount of a compound of formula I, or a pharmaceutically acceptable salt thereof, and a pharmaceutically acceptable carrier.

Preferred embodiments of the present invention include the compounds of formula I in which:

(A) R1 and R2 are independently methyl;
  $X_1$ is C(=NR5)-NR6R7; and
  n is one.

(B) R1 and R2 are independently methyl;
  $X_1$ is a heteroaryl ring as previously defined; and
  n is one.

The most preferred embodiment of the present invention includes the compounds of formula I in which:

R1 and R2 are each methyl;

R3 is hydrogen;

$X_1$ is a heteroaryl ring as previously defined;

$X_2$ is 4-fluoro; and n is one.

A preferred compound of formula I in accordance with the present invention is:

2-(1-[3-(methylamino)propyl]-1-(4-fluorophenyl)-1,3-dihydro-2-benzofuran-5-yl])-1H-imidazole.

Other preferred compounds of the general formula I include the following:

2-(1-[3-(dimethylamino)propyl]-1-(4-fluorophenyl)-1,3-dihydro-2-benzofuran-5-yl])-1,3-thiazole;

2-(1-[3-(dimethylamino)propyl]-1-(4-fluorophenyl)-1,3-dihydro-2-benzofuran-5-yl])-1,3-oxazole;

4-(1-[3-(dimethylamino)propyl]-1-(4-fluorophenyl)-1,3-dihydro-2-benzofuran-5-yl])-1,3-thiazole;

2-(1-[3-(dimethylamino)propyl]-1-(4-fluorophenyl)-1,3-dihydro-2-benzofuran-5-yl])-1,3-thiazole;

3-(1-[3-dimethylamino)propyl]-1-(4-fluorophenyl)-1,3-dihydro-2-benzofuran-5-yl])-1,2-isothiazole;

4-(1-[3-(dimethylamino)propyl]-1-(4-fluorophenyl)-1,3-dihydro-2-benzofuran-5-yl])-2-methyl-1H-midazole;

5-(1-[3-(dimethylamino)propyl]-1-(4-fluorophenyl)-1,3-dihydro-2-benzofuran-5-yl])-2,4-dimethyl-1H-imidazole;

2-(1-[3-(dimethylamino)propyl]-1-(4-fluorophenyl)-1,3-dihydro-2-benzofuran-5-yl])-1H-1,3,4-triazole;

2-(1-[3-(dimethylamino)ethyl]-1-(4-fluorophenyl)-1,3-dihydro-2-benzofuran-5-yl])-1H-imidazole;

2-(1-[3-(dimethylamino)butyl]-1-(4-fluorophenyl)-1,3-dihydro-2-benzofuran-5-yl])-1H-imidazole;

2-(1-[3-(dimethylamino)propyl]-1-(4-fluorophenyl)-1,3-dihydro-2-benzofuran-5-yl])-4-methyl-1H-imidazole;

5-(1-[3-(dimethylamino)propyl]-1-(4-fluorophenyl)-1,3-dihydro-2-benzofuran-5-yl])-1H-tetrazole;

1-(1-[3-(dimethylamino)propyl]-1-(4-fluorophenyl)-1,3-dihydro-2-benzofuran-5-yl])-5-methyl-2H-tetrazole;

3-(1-[3-(dimethylamino)propyl]-1-(4-fluorophenyl)-1,3-dihydro-2-benzofuran-5-yl])-1,2,4-thiadiazole;

3-(1-[3-(dimethylamino)propyl]-1-(4-fluorophenyl)-1,3-dihydro-2-benzofuran-5-yl])-1,2,4-oxadiazole;

1-methyl-2-(1-[3-(dimethylamino)propyl]-1-(4-fluorophenyl)-1,3-dihydro-2-benzofuran-5-yl])-1H-imidazole.

4-methyl-2-(1-[3-(dimethylamino)propyl]-1-(4-fluorophenyl)-1,3-dihydro-2-benzofuran-5-yl])-1H-imidazole.

2(S)-2-(1-[3-(dimethylamino)propyl]-1-(4-fluorophenyl)-1,3-dihydro-2-benzofuran-5-yl])-1H-imidazole.

2(R)-2-(1-[3-(dimethylamino)propyl]-1-(4-fluorophenyl)-1,3-dihydro-2-benzofuran-5-yl])-1H-imidazole.

2-(1-[3-(dimethylamino)propyl]-1-(4-fluorophenyl)-1,3-dihydro-2-benzofuran-5-yl])-1H-benzimidazole;

4,5-dimethyl-2-(1-[3-(dimethylamino)propyl]-1-(4-fluorophenyl)-1,3-dihydro-2-benzofuran-5-yl])-1H-imidazole;

2-[1-[3-(dimethylamino)propyl]-1-(4-fluorophenyl)-1,3-dihydro-2-benzofuran-5-yl]-1,2,3,4-tetrahydro-1H-isoquinolin-2-yl)methanimine;

2-(1-[3-dimethylaminopropyl]-1-(4-fluorophenyl)-1,3-dihydro-2-benzofuran-5-yl})-1,3-pyrimidine;

3-(1-[3-dimethylaminopropyl]-1-(4-fluorophenyl)-1,3-dihydro-2-benzofuran-5-yl})-1,2,4-triazine;

2-(1-[3-(dimethylamino)propyl]-1-(4-fluorophenyl)-1,3-dihydro-2-benzofuran-5-yl)-1H-4,5-dihydroimidazole;

2-(1-[3-(dimethylamino)propyl]-1-(4-fluorophenyl)-1,3-dihydro-2-benzofuran-5-yl)-4,5,6,7-tetrahydro-1H-1,3-diazepine; and 2-(1-[3-(dimethylamino)propyl]-1-(4-fluorophenyl)-1,3-dihydro-2-benzofuran-5-yl)-1,4,5,6-tetrahydro-pyrimidine.

The most preferred compounds of the invention include:

2-(1-[3-(dimethylamino)propyl]-1-(4-fluorophenyl)-1,3-dihydro-2-benzofuran-5-yl])-1H-imidazole.

A preferred use for compounds of formula I is the treatment of pain. More specifically, the compounds of formula I are expected to be useful in the treatment of chronic pain from cancer, post-traumatic nerve damage, diabetic neuropathy, chronic primary pain, fibromyalgia, post-surgical pain, chronic visceral pain, chronic headache, orofacial disorders, musculoskeletal disorders, spinal cord injury and musculoskeletal pain.

DETAILED DESCRIPTION OF THE INVENTION

The compounds of formula I may be prepared as described in the following reaction schemes and discussions. Unless otherwise indicated, $X_1$, $X_2$, R1, R2, R3, R4, R5, R6, R7, R8 and R9, and structural formulae II, III, IV, VI, VIIa, VIIb, VIII, IX in the reaction schemes and discussion that follow are as defined above.

Scheme 1

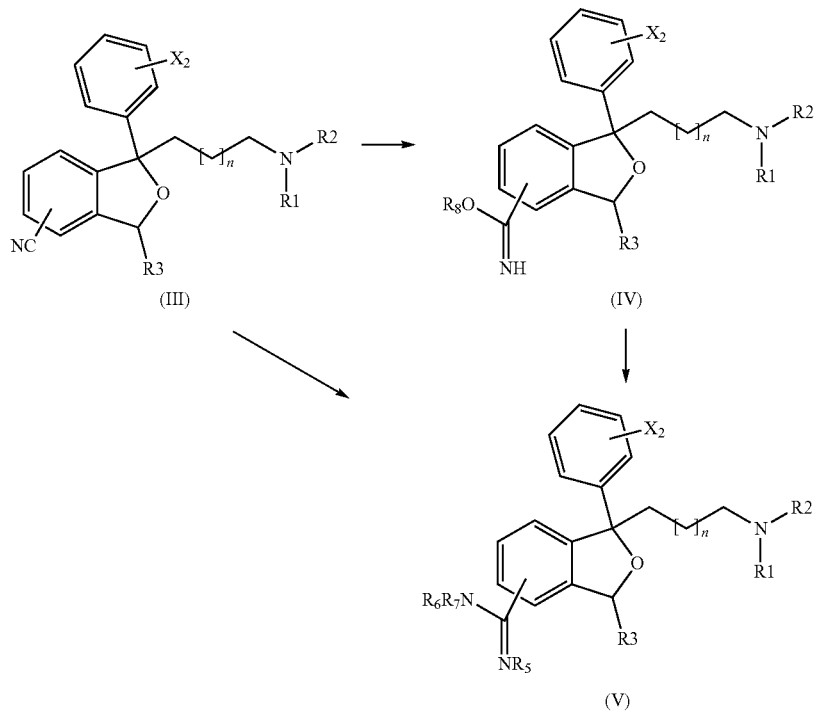

According to Scheme 1, compounds of the general formula III may be converted to an imino-ether (i.e., imidate) of the general formula IV, and next converted to an amidine of the general formula V using the appropriate primary or secondary amine HNR6R7. One efficient method for this process is via the Pinner reaction, which involves treatment of the nitrile of formula III with an acid, preferably hydrochloric acid, and a low molecular weight alcohol $R_8OH$ such as methanol or ethanol, preferably ethanol, at a temperature in the range from about 0° C. to about the boiling point of the alcohol used, preferably at about 80° C. for ethanol, and at a pressure of about one to three atmospheres, preferably at atmospheric pressure, to generate the intermediate imino-ether IV. The crude intermediate IV can then be reacted with an appropriate amine of the general formula HNR6R7 present in a ratio of 0.5 to 5 equivalents, preferably in a ratio of 1 to 3 equivalents, to produce the amidine compounds of general formula V (i.e., general formula I where $X_1$ is —C(=NR5)-NR6R7, i.e., formula II). This process is described in a number of organic syntheses texts, including Jie Jack Li, *Name Reactions: A Collection of Detailed Mechanisms and Synthetic Applications* ($4^{th}$ Ed.), pp. 438-9, Springer-Verlag, New York, 2009). Additional examples of the Pinner reaction and modifications can be found in Saul Patai, *The Chemistry of Amidines and Imidates*, Wiley, New York, 1975, pp.385-489. Another useful review is by R. Roger and D. Neilson, *Chemical Reviews*, 1961, 61(2), 179-211.

The starting materials for this process, compounds of the general formula III, are available using procedures described in the chemical and patent literature. For example, the compound of formula III, wherein n=1, R1=CH3, R2=CH3, R3=H, $X_2$ is 4-fluoro and the CN group is attached to the 5-position of the benzofuran ring has been commercially available as the antidepressant citalopram (in racemic form) and as the antidepressant escitalopram (as the single, (S)-isomer). Procedures for the syntheses of these compounds are also readily available in the literature (e.g., see M. Pitts, *Tetrahedron*, 2006, 62, 4705-4708; N. Periyandi, et al, PCT Int. Appl., (2006), WO-2006021971; T. Ikemoto and Y. Watanabe, PCT Int. Appl., (2005), WO-2005082842; H. Ahmadian and H. Petersen, PCT Int. Appl., (2003), WO-2003051861; H. Petersen, PCT Int. Appl. (2001), WO-2001068631; L. Dall'Asta, et al, PCT Int. Appl., (2000), WO-2000023431).

Alternatively, the imino-ether of general formula IV may be isolated, e.g. as a hydrochloride salt, which may be converted to the free imino-ether by treatment with a weak base such as sodium bicarbonate, or purified and subsequently reacted with the appropriate amine of general formula HNR6R7 to generate the desired product of general formula V.

In some cases, it may also be desirable to convert the nitrile group of the compound of formula II directly into the amidine group present in the compound of formula V (i.e., compound of formula I wherein $X_1$ is —C(=NR5)—NR6R7). Examples of this process are found in G. Rousselet, et al, *Tetrahedron Letters*, 1993, 34 (40), 6395-6398, and R. Garigipati, *Tetrahedron Letters*, 1990, 31 (4), 1969-1972.

According to Scheme 2, a compound of the general formula III, may be converted directly into an amidine of general formula V using an excess of ammonia under conditions normally employed in the Pinner reaction (see above). These simple amidines of general formula VI can then be converted to the desired compounds of general formula V (i.e., general formula I wherein $X_1$ is a heterocyclic ring, including imidazole). Procedures for this conversion may be found in the chemical literature and are familiar to one skilled in the art of organic synthesis. For example, conversion of intermediate VI, wherein R1 and R2 are methyl, R3 is hydrogen, n equals 1 and $X_2$ is 4-fluoro, to a compound of general formula V can be accomplished using an amino-acetal, followed by ring closure to produce the heterocyclic imidazole ring (e.g., see R. Frutos, et al *Tetrahedron Letters*, 2005, 46(48), 8369-8372). Other heterocyclic ring systems that can be prepared in this manner include, for example, benzimidazolyl and 1,3-pyrimidinyl.

Scheme 2

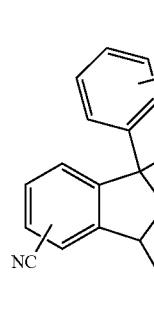

(III)

(VI)

(V)

In another embodiment, the nitrile compound of formula III can be reacted with e.g., sodium azide to directly generate a tetrazole derivative of general formula I, wherein $X_1$ is:

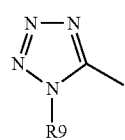

(VIIa)

and R9 is H or $C_1$-$C_3$ alkyl (see, for example, B. Das, et al, *Synlett*, 2010, 391-394; J. Roh, et al, *Synthesis*, 2009, 2175-2178; D. Cantillo, et al, *Journal of the American Chemical Society*, 2011, 133, 4465-4475; W.-K. Su, *European Journal of Organic Chemistry*, 2006, 2723-2726.

Scheme 3

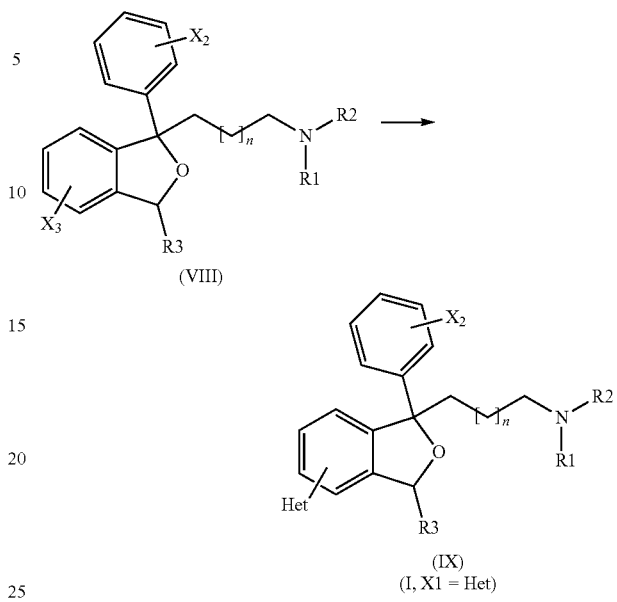

(VIII)

(IX)
(I, X1 = Het)

In another embodiment, an intermediate of the general formula VIII, wherein X3 is as defined below, can be converted into a compound of the general formula IX (i.e., general formula I, wherein $X_1$ is a heteroaryl group, using one or more of a variety of methods described in the chemical literature. This can be accomplished via a process referred to as a Suzuki (or Suzuki-Miyaura) coupling reaction (e.g., see K. Wong, et al, *Journal of Organic Chemistry*, 2002, 67 (3), 1041-1044). The reaction typically employs a palladium catalyst to couple an aryl halide with an aryl, or heteroaryl, boronic acid or boronate ester. Examples of this reaction can be found in, for example, L. Wang, et al, *European Journal of Organic Chemistry*, 2012, (3), 595-603; M. Li, et al, *Tetrahedron Letters*, 2009, 50 (13), 1478-1481; J. C. W. Evans, et al, *Organic Synthesis*, 1938, 18. Modifications to this coupling process include the use of other metals, such as magnesium (for the preparation of 1,2,3-triazines—see, A. Ohsawa, et al, *Journal of the Chemical Society, Chemical Communications*, 1985, (20), 1370); cesium and copper (I) (see H. Yang, et al, *Letters in Organic Chemistry*, 2011, 8 (5), 325-331; C. Cao, et al, *Synthetic Communications*, 2012, 42 (2), 279-284) and microwave conditions (see H. Huang, *Journal of Combinatorial Chemistry*, 2008, 10 (5), 617-619). A modification of the Ullmann reaction to prepare substituted 1,2,4-triazoles has also been described (see P. Suresh, et al, *Journal of Organic Chemistry*, 2008, 73(22), 9121-9124).

The starting materials for this process, compounds of the general formula VIII, wherein $X_3$ is, e.g., chlorine, bromine or iodine, are described in the chemical literature, or may be commercially available (e.g., see J. Eildal, et al, *Journal of Medicinal Chemistry*, 2008, 51, 3045). The aryl, or heteroaryl, boronic acids or esters may be obtained from commercial sources (e.g., Sigma-Aldrich Chemical, St. Louis, Mo.), or prepared as described in the chemical literature (e.g., see P. Zhang, et al, *Journal of Medicinal Chemistry*, 2010, 53, 6112-6121; P. Bartlett, et al *Chemical Reviews*, 1997, 97, 1281; R. Batey, et al, *Journal of the American Chemical Society*, 1999, 121, 5075; J. Bird, et al, *Journal of Medicinal Chemistry*, 1994, 37, 158).

Where cis- and trans-isomers are possible for an embodiment of the inventive compounds of formula I, both cis- and trans-isomers (i.e., diastereomers) are within the scope of this invention. Similarly, when R- and S-, or (+)- and (−)-, or d- and l-isomers (i.e., enantiomers) are possible for an embodiment of the inventive compounds of formula I, each and every one of said isomers are within the scope of this invention.

The term "alkyl" refers to straight or branched chains of carbon atoms. Exemplary alkyl groups are $C_3$-$C_{10}$ alkyl groups which include methyl, ethyl, propyl, isopropyl, butyl, isobutyl, pentyl, isopentyl, hexyl and the like, including all regioisomeric forms thereof, and straight and branched chain forms thereof. The term "alkyl" is also used to denote straight or branched chains of carbon atoms having one or more carbon-carbon double bonds, such as vinyl, allyl, butenyl and the like, as well as straight and branched chains of carbon atoms having one or more carbon-carbon triple bonds, such as ethynyl, propargyl, butynyl, and the like.

The term "aryl" denotes a cyclic, aromatic hydrocarbon. Examples include phenyl, naphthyl, anthracenyl, phenanthracenyl, and the like.

The terms "alkoxy" and "aryloxy" denote "O-alkyl" and "O-aryl", respectively. The term "cycloalkyl" denotes a cyclic group of carbon atoms, where the ring formed by the carbon atoms may be saturated or may comprise one or more carbon double bonds in the ring. Examples of cycloalkyl groups include cyclopropyl, cyclobutyl, cyclopentyl, cyclohexyl, cycloheptyl, and the like as well as cyclopentenyl, cyclopentadienyl, cyclohexenyl, cyclohexadienyl, and the like. As used herein, the term "cycloalkyl" is also intended to denote a cyclic group comprising at least two fused rings, such as adamantyl, decahydronaphthalinyl, norbornanyl, where the cyclic group may also have one or more carbon-carbon double bonds in one or more rings, such as in bicyclo(4.3.0)nona-3,6(1)-dienyl, dicyclopentadienyl, 1,2,3,4-tetrahydronaphthalinyl(tetralinyl), indenyl, and the like.

The term "one or more substituents" as used herein, refers to a number of substituents that equals from one to the maximum number of substituents possible based on the number of available bonding sites.

The terms "halo" and "halogen", as used herein, unless otherwise indicated, include chloro, fluoro, bromo and iodo.

The term "heteroaryl" denotes a monocyclic or bicyclic aromatic group wherein one or more carbon atoms are replaced with heteroatoms selected from the group consisting of nitrogen, oxygen and sulfur. If the heteroaryl group contains more than one heteroatom, the heteroatoms may be the same or different. Preferred heteroaryl groups are five- to fourteen-member rings that contain from one to four heteroatoms independently selected from oxygen, nitrogen and sulfur. Examples of preferred heteroaryl groups include benzo[b]thienyl, chromenyl, furyl, imidazolyl, indazolyl, indolizinyl, indolyl, isobenzofuranyl, isoindolyl, isoquinolinyl, isothiazolyl, isoxazolyl, napthylidinyl, oxadiazolyl, oxazinyl, oxazolyl, phthalazinyl, pteridinyl, purinyl, pyranyl, pyrazinyl, pyrazolyl, pyridazinyl and pyridinyl.

The term "treating", as used herein, refers to reversing, alleviating, inhibiting the progress of, or preventing the disorder or condition to which such term applies, or preventing one or more symptoms of such disorder or condition. The term "treatment", as used herein, refers to the act of treating, as "treating" is defined immediately above.

The compounds of formula I of the present invention may also contain functional groups or heterocyclic ring systems that may exist in one or more tautomeric forms. The present invention includes within its scope all such tautomeric forms, including mixtures of such forms.

The compounds of the present invention may have optical centers and therefore may occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or any of its intermediates.

The compounds of formula I may also exist in the form of cis- or trans-isomers with respect to configuration on the furan ring of formula I. Such cis- and trans-isomers are also considered to be within the scope of the present invention, The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, phosphorus, fluorine, and chlorine, such as $^2H$, $^3H$, $^{11}C$, $^{13}C$, $^{14}C$, $^{13}N$, $^{15}N$, $^{17}O$, $^{18}O$, $^{35}S$, $^{31}P$, $^{32}P$, $^{31}P$, $^{18}F$ and $^{37}Cl$, respectively. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with isotopes such as deuterium, i.e., $^2H$, can afford certain therapeutic advantages resulting from greater metabolic stability, for example increased in vivo half-life or reduced dosage requirements and hence may be preferred in some circumstances. Isotopically labeled compounds of formula I of this invention and prodrugs thereof can generally be prepared by carrying out the procedures disclosed in the Schemes and/or the examples and Preparations below, by substituting a readily available isotopically labeled reagent for a non-isotopically labeled reagent.

Compounds of the present invention, prodrugs thereof and pharmaceutically acceptable salts of said compounds, or of said prodrugs which contain the aforementioned isotopes and/or other isotopes of other atoms, are within the scope of this invention.

A "unit dosage form" as used herein is any form that contains a unit dose of the compound of formula I. A unit dosage form may be, for example, in the form of a tablet or a capsule. The unit dosage form may also be in liquid form, such as a solution or suspension.

The compositions of the present invention may be formulated in a conventional manner using one or more pharmaceutically acceptable carriers. Thus, the active compounds of the present invention may be formulated for oral, buccal, intranasal, parenteral (e.g., intravenous, intramuscular or subcutaneous) or rectal administration or in a form suitable for administration by inhalation or insufflations.

For oral administration, the pharmaceutical compositions may take the form of, for example, tablets or capsules prepared by conventional means with pharmaceutically acceptable excipients such as binding agents (e.g., pre-gelatinized maize starch, polyvinylpyrrolidone or hydroxypropyl methylcellulose); fillers (e.g., lactose, microcrystalline cellulose or calcium phosphate); lubricants (e.g., magnesium stearate, talc, or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispensing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrachloroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parenteral or buccal administration to the average adult human for the treatment of the conditions referred to above is from about 0.1 mg/kg to about 100 mg/kg of the active ingredient per unit dose which could be administered, for example, one to four times per day. Toxicity concerns at the higher level may restrict intravenous (i.v.) dosages to a lower level, such as up to about 10 mg/kg. A dose of about 0.1 mg/kg to about 100 mg/kg may be employed for oral (p.o.) administration. Typically, a dosage from about 0.1 mg/kg to about 10 mg/kg may be employed for intramuscular (i.m.) injection. Preferred dosages are in the 1.0 mg/kg to about 100 mg/kg range, and more preferably in the 5 mg/kg to about 50 mg/kg range for i.v. or p.o. administration. The duration of the treatment is usually once per day for a period of three days to three weeks, or until the condition is essentially controlled. Lower doses given less frequently can be used prophylactically to prevent or reduce the incidence of recurrence of the infection.

Aerosol formulations for treatment of the conditions referred to above in the average human are preferably arranged such that each metered dose or "puff" of aerosol contains 0.1 micrograms to 100 micrograms of the compound of the invention. The overall daily dose with an aerosol will be within the range of 0.1 mg/kg to about 100 mg/kg, and preferably in the range of 1.0 mg/kg to about 25 mg/kg. Administration may be several times daily, for example 2, 3, 4 or 8 times, giving for example 1, 2 or 3 doses each time.

Examples of the disorders or conditions which may be treated by a compound, composition and method of this invention chronic pain from cancer, post-traumatic nerve damage, diabetic neuropathy, chronic primary pain, fibromyalgia, post-surgical pain, chronic visceral pain, chronic headache, orofacial disorders, musculoskeletal disorders, spinal cord injury and musculoskeletal pain.

As an example, the mammal in need of treatment or prevention may be a human. As another example, the mammal in need of treatment or prevention may be a mammal other than a human.

In so far as the compounds of formula I of this invention are basic compounds, they are capable of forming a variety of different salts with various inorganic and organic acids. Although such salts must be pharmaceutically acceptable for administration to animals, including humans, it is often desirable in practice to initially isolate the base compound from the reaction mixture as a pharmaceutically unacceptable salt, then isolate the base by treatment of the salt with an alkaline reagent and finally convert the isolated free base compound to a pharmaceutically acceptable acid addition salt.

The acids which are used to prepare the pharmaceutically acceptable acid salts of the active compound used in formulating the pharmaceutical composition of this invention that are basic in nature are those which form non-toxic acid addition salts, e.g., salts containing pharmacologically acceptable anions. Non-limiting examples of the salts include the acetate, benzoate, beta-hydroxybutyrate, bisulfate, bisulfite, bromide, butyne-1,4-dioate, caproate, chloride, chlorobenzoate, citrate, dihydrogen phosphate, dinitrobenzoate, fumarate, glycollate, heptanoate, hexyne-1,6-dioate, hydroxybenzoate, iodide, lactate, maleate, malonate, mandelate, metaphosphate, methanesulfonate, methoxybenzoate, monohydrogen phosphate, naphthalene-1-sulfonate, naphthalene-2-sulfonate, oxalate, phenylbutyrate, phenylpropionate, phosphate, phthalate, phenylacetate, propanesulfonate, propiolate, propionate, pyrophosphate, pyrosulfate, sebacate, suberate, succinate, sulfate, sulfite, sulfonate, tartrate, xylenesulfonate, trifluoroacetate, acid phosphate, acid citrate, bitartrate, succinate, gluconate, saccharate, nitrate, methanesulfonate, and pamoate {i.e., 1,1'-methylene-bis-(2-hydroxy-3-naphthoate)] salts.

Also included within the scope of this invention are solvates and hydrates of compounds of formula I and their pharmaceutically acceptable salts. The present invention includes within its scope all possible stoichiometric and non-stoichiometric forms.

In the examples that follow, the abbreviations used are intended to have the following, general meaning:
    bm: broad multiplet (NMR)
    bs: broad singlet (NMR)
    d: doublet (NMR)
    dd: doublet of doublets (NMR)
    d.e.: diatomaceous earth, filtering agent
    calcd.: calculated value
    equiv: equivalent J: coupling constant (NMR)
HPLC: high pressure liquid chromatography
LC: liquid chromatography
m: multiplet (NMR)
min: minute(s)
m/z: mass to charge ratio (mass spectroscopy)
obsd: observed value
Rf: retention factor (chromatography)
RT: retention time (chromatography)
rt: room temperature (typically 25° C.)
s: singlet (NMR)
t: triplet (NMR),
T: temperature
tlc: thin layer chromatography
TFA: trifluoroacetic acid
THF: tetrahydrofuran Solvents were purchased and used without purification. Yields were calculated for material judged homogeneous by thin layer chromatography and NMR. Thin layer chromatography was performed on Kieselgel plates eluting with the indicated solvents, visualized by using a 254 nm UV lamp, or stained with an aqueous $KMnO_4$ solution, an ethanolic solution of 12-molybdophosphoric acid.

Nuclear Magnetic Resonance (NMR) spectra were acquired on 90- or 400-MHz NMR Spectrometers. Chemical shifts for proton (i.e., $^1H$) NMR spectra are reported in parts per million (ppm) relative to the singlet of $CDCl_3$ at 7.24 ppm.

Conditions for High Pressure Liquid Chromatography-Mass Spectrometry (HPLC-MS) Analysis:
Column: Zorbax RRHD Eclipse Plus (Agilent) $C_{18}$, 1.9 micron, 50 mm×2.1 mm
Eluent I.
A: Acetonitrile-$H_2O$=5:95, 20 mM $HCOONH_4$/$NH_4OH$ buffer, pH 7.4
B: Acetonitrile-$H_2O$=80:20, 20 mM $HCOONH_4$/$NH_4OH$ buffer, pH 7.4
Eluent II.
A: $H_2O$ with 0.1% TFA, pH 2.2
B: Acetonitrile with 0.1% TFA, pH 2.2
Gradient program: adjusted according to the compound properties; typically, start: 0% B to 100% B in 1 minute, 0.8 minute isocratic B.
Column Temp.: 40° C.
Flow Rate: 0.6 mL/min
Sample Conc.: ca. 1 mg/mL
Sample Solvent: Acetonitrile
Injection: 0.5 µL
Detection wavelength: 220 nm
Mass Spectrum (MS) Conditions:
Measured Mass Range: 100-750 Daltons
Scan Time: 0.2 s
Ion mode: ES±
Cone Voltage: 20 V
Capillary Voltage: 3 V
Source temp.: 140° C.
Desolvation temp.: 450° C.
Desolvation gas: 450 L/h
Cone gas: 60 L/h

EXAMPLE 1

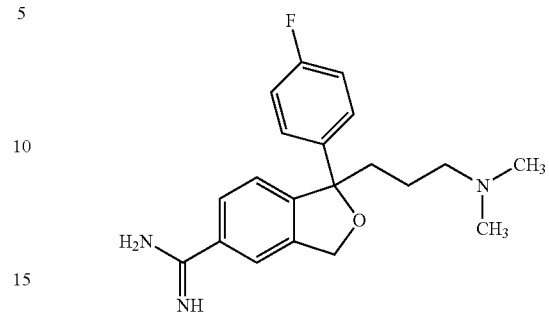

1-[3-(dimethylamino)propyl]-1-(4-fluorophenyl)-1,3-dihydro-2-benzofuran-5-carboximid-amide A mixture of 1-[3-(dimethylamino)propyl]-1-(4-fluorophenyl)-1,3-dihydro-2-benzofuran-5-carbonitrile hydrobromide (citalopram hydrobromide, 300 mg, 1.0 equiv), copper (II) chloride (1.5 equiv) and ammonia (2.8 equiv) in ethanol (6 mL) was heated at 80° C. for 48 h. The mixture was cooled to room temperature and concentrated to dryness to give crude product (M/Z 342 [M$^+$+H]). This material was purified by re-suspending the crude product in fresh ethanol, filtration to remove insoluble material and slow evaporation under N2 to give the title product, 90 mg (23%) of a pale yellow powder.

LC : 97%;

MS: calcd. for $C_{20}H_{24}FN_3O$: 341.2; obsd. 342 (M$^+$+H).

The following compounds 2 through 8 were also prepared using the general procedure as described for the title compound of Example 1.

EXAMPLE 2

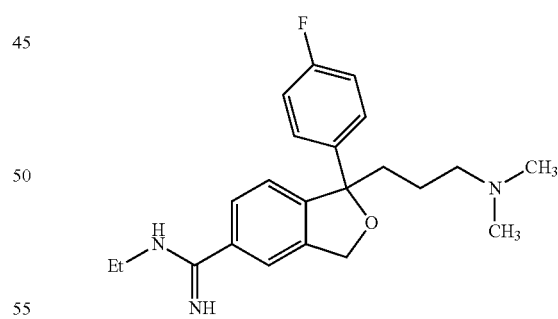

N-ethyl-1-[3-(dimethylamino)propyl]-1-(4-fluorophenyl)-1,3-dihydro-2-benzofuran-5-car-boximidamide Using 250 mg of 1-[3-(dimethylamino)propyl]-1-(4-fluorophenyl)-1,3-dihydro-2-benzofuran-5-carbonitrile hydrobromide (citalopram HBr, 1.0 equiv) and ethylamine (1.3 equiv) gave, after heating at 80° C. for 15 h, the title product (65 mg, 19% yield) as a white solid.

LC: 91%;

MS: calcd. for $C_{22}H_{28}FN_3O$: 369.2; obsd. 370 (M$^+$+H).

EXAMPLE 3

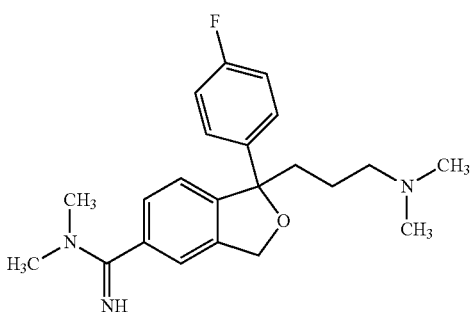

N,N-dimethyl-1-[3-(dimethylamino)propyl]-1-(4-fluorophenyl)-1,3-dihydro-2-benzofuran-5-carboximidamide Using 300 mg of 1-[3-(dimethylamino)propyl]-1-(4-fluorophenyl)-1,3-dihydro-2-benzofuran-5-carbonitrile hydrobromide (citalopram HBr) and dimethylamine (1.3 equiv) gave, after heating at 80° C. for 14 h, title product (90 mg, 26% yield) as a light yellow semisolid.

LC: 99%;

MS: calcd. for $C_{22}H_{28}FN_3O$: 369.2; obsd. 370 (M$^+$+H).

EXAMPLE 4

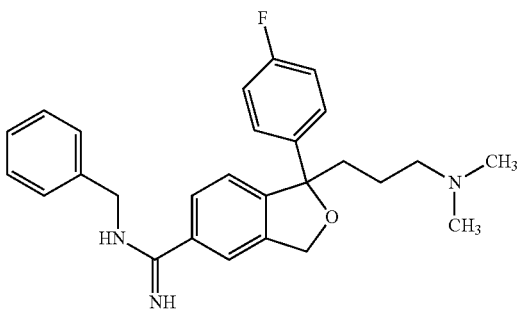 [SMILES: CN(C)CCCC1(c2ccc(F)cc2)OCc2cc(C(=N)NCc3ccccc3)ccc21]

N-benzyl-1-[3-(dimethylamino)propyl]-1-(4-fluorophenyl)-1,3-dihydro-2-benzofuran-5-carboximidamide Using 250 mg of 1-[3-(dimethylamino)propyl]-1-(4-fluorophenyl)-1,3-dihydro-2-benzofuran-5-carbonitrile hydrobromide (citalopram HBr) and benzylamine (1.2 equiv) gave, after heating at 80° C. for 14 h, title product (72 mg, 19% yield) as a white solid.

LC: 97%;

MS: calcd. for $C_{27}H_{30}FN_3O$: 431.2; obsd. 432 (M$^+$+H).

EXAMPLE 5

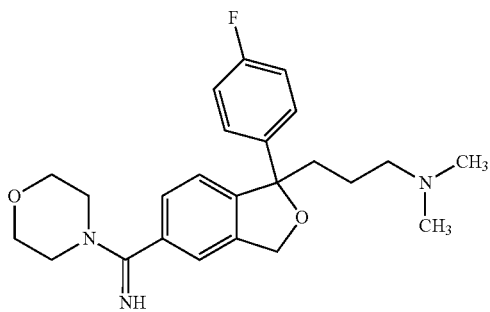 [SMILES: CN(C)CCCC1(c2ccc(F)cc2)OCc2cc(C(=N)N3CCOCC3)ccc21]

1-[1-[3-(dimethylamino)propyl]-1-(4-fluorophenyl)-1,3-dihydro-2-benzofuran-5-yl]-1-(morpholine-4-yl)-methanimine Using 400 mg of 1-[3-(dimethylamino)propyl]-1-(4-fluorophenyl)-1,3-dihydro-2-benzofuran-5-carbonitrile hydrobromide (citalopram HBr) and morpholine (1.5 equiv) gave, after heating at 80° C. for 28 h, title product (75 mg, 15% yield) as a white solid.

LC: 96.9%;

MS: calcd. for $C_{24}H_{30}FN_3O_2$: 411.2; obsd. 412 (M$^+$+H).

EXAMPLE 6

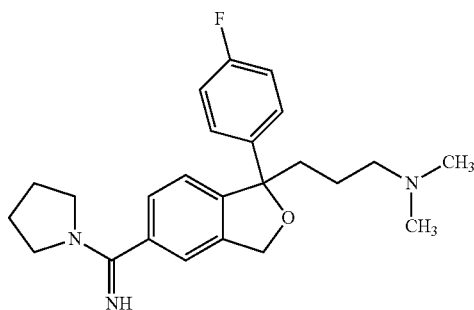 [SMILES: CN(C)CCCC1(c2ccc(F)cc2)OCc2cc(C(=N)N3CCCC3)ccc21]

1-[1-[3-(dimethylamino)propyl]-1-(4-fluorophenyl)-1,3-dihydro-2-benzofuran-5-yl]-1-(pyrrolidin-1-yl)-methanimine Using 100 mg of 1-[3-(dimethylamino)propyl]-1-(4-fluorophenyl)-1,3-dihydro-2-benzofuran-5-carbonitrile hydrobromide (citalopram HBr) and pyrrolidine (1.2 equiv) gave, after heating at 80° C. for 14 h, title product (58 mg, 40% yield) as a light yellow solid.

LC: 91%;

MS: calcd. for $C_{24}H_{30}FN_3O.2HCl$: 395.2; obsd. 396 (M$^+$+H).

$^1$H-NMR (DMSO-$d_6$, 400 MHz, T=30° C.) δ 1.52 (m, 2H), 1.85 (m, 2H), 2.05 (m, 2H), 2.20 (m. 2H), 2.35 (m, 2H), 2.65 (s, 6H), 3.05 (m, 2H), 3.38 (m, 2H), 3.53 (m, 2H), 5.22 (q, 2H), 7.18 (m, 2H), 7.60 (m, 4H), 7.75 (d, 1H), 8.80 (s, 1H), 9.22 (s, 1H), 10.15 (bs, 1H).

EXAMPLE 7

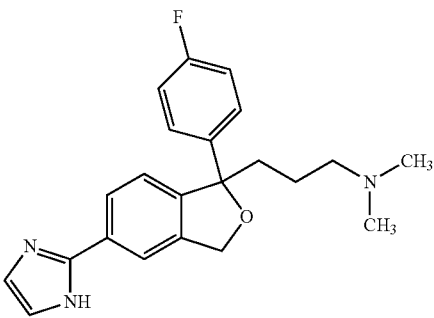 [SMILES: CN(C)CCCC1(c2ccc(F)cc2)OCc2cc(-c3ncc[nH]3)ccc21]

2-(1-[3-(dimethylamino)propyl]-1-(4-fluorophenyl)-1,3-dihydro-2-benzofuran-5-yl])-1H-imidazole 1-[3-(dimethylamino)propyl]-1-(4-fluorophenyl)-1,3-dihydro-2-benzofuran-5-carbonitrile hydrobromide (citalopram HBr, 300 mg, 1.0 equiv.) was converted to its free base using saturated aqueous Na$_2$CO$_3$ and EtOAc. The resulting oil was combined with copper(I) chloride (1.5 equiv.) in anhydrous ethanol (6 mL), treated with aminoacetaldehyde diethylacetal (1.3 equiv., Aldrich Chemical Co.) and heated under $N_2$ at 80° C. for 14 hr. Without purification, the mixture containing the intermediate acetal was treated with ethanol (8 mL) and 6N HCl (2 mL) at 80° C. for 2 hr. The reaction mixture was cooled to room temperature, the solvent removed in vacuo and the residue purified by re-suspending the crude product in fresh ethanol, filtration to remove insoluble material and slow evaporation under $N_2$ to produce the title product, 65 mg (12%) as a light yellow solid.

LC: 96.1%;

MS: calcd. for $C_{22}H_{24}FN_3O$: 365.2; obsd. 366 (M$^+$+H).

$^1$H-NMR (DMSO-d$_6$, 400 MHz, T=30° C.) δ1.34-1.71 (m, 2H), 2.25 (m, 2H), 2.65 (s, 6H), 3.05 (m, 2H), 5.25 (q, 2H), 7.18 (m, 2H), 7.62 (m, 2H), 7.75 (m, 2H), 7.85 (m, 1H), 8.05 (m, 1H), 8.12 (m, 1H), 10.0 (bs, 1H), 14.9 (bs, 1H).

Opioid Receptor Affinity

The compounds were tested for activity vs. opioid receptor subtypes Kappa (KOR), Delta (DOR) and Mu (MOR) at an initial concentration of 10 μM each, through the NIMH Psychoactive Drug Screening Program (PDSP), operated by Dr. Bryan Roth and his colleagues in the Department of Pharmacology at the University of North Carolina (Chapel Hill, N.C.) through an agreement with the National Institute of Mental Health (NIMH). Human KOR, DOR and MOR were expressed in CHO cells for each assay.

Data

| Example | KOR Ki, nM [or % inh. at 10 uM] | DOR Ki, nM [or % inh. at 10 uM] | MOR Ki, nM [or % inh. at 10 uM] |
|---|---|---|---|
| 4 | 30 | [10%] | [39%] |
| 6 | 249 | [6%] | [8%] |
| 7 | 47 | [24%] | [39%] |

What we claim:

1. A method of treatment of a disorder or condition in a mammal, selected from the group consisting of chronic cancer pain, pain from post-traumatic nerve damage, diabetic neuropathy pain, chronic primary pain, fibromyalgia, post-surgical pain, chronic visceral pain, chronic headache, pain from orofacial disorders, pain from musculoskeletal disorders, spinal cord injury pain and musculoskeletal pain, the method comprising administering to a mammal in need of such treatment a therapeutically effective amount of a compound of the formula (I):

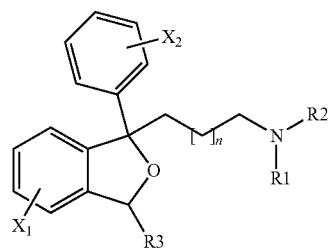

or a pharmaceutically acceptable salt thereof, wherein:

$X_1$ is a group of the general formula (II):

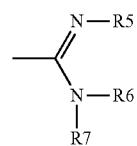

or $X_1$ is a heteroaryl ring, selected from the list consisting of 2-imidazolyl, 4-imidazolyl, 2-thiazolyl, 4-thiazolyl, 5-thiazolyl, 2-oxazolyl, 4-oxazolyl, 5-oxazolyl, 1,2,4-thiadiazol-3-yl, 1,2,4-thiadiazol-2-yl, 1,2,4-thiadiazol-4-yl, 1,2,3-triazolyl-2-yl, 1,2,3-triazol-1-yl, 1,2,4-triazol-1-yl, 1,2,4-triazol-3-yl,1,2,4-triazol-4-yl, 1,3-thiazol-2-yl, 1,3-thiazol-4-yl, 1,2,3,4-tetrazol-5-yl, 1,2,3,4-tetrazol-1-yl, 1,2,4-oxadiazol-3-yl, 1,2,4-oxadiazol-2-yl, 1,2,4-oxadiazol-3-yl, 1,2,4-oxadiazol-5-yl, 1,3-pyrimidin-2-yl, 1,2-pyrazin-3-yl and 1,2,4-triazin-3-yl;

R5, R6 and R7 are independently selected from the list consisting of H, $C_1$-$C_6$ alkyl, $C_3$-$C_7$-cycloalkyl, aryl and heteroaryl; or R5 and R6, taken together with the N—C═N group to which they are attached, form a 4-10 membered cyclic or bicyclic ring, wherein up to two carbon atoms are replaced with heteroatoms selected from the group consisting of N, O and S; or R6 and R7 taken together with the nitrogen atom to which they are attached form a 4-10 membered cyclic or bicyclic ring, wherein up to two carbon atoms are replaced with heteroatoms selected from the group consisting of N, O and S or form a ring selected from azetidine, pyrrolidine, piperidine, azepine, piperazine, morpholine, thiomorpholine, oxazole and thiazole;

$X_2$ is H, Br, Cl or F;

R1 and R2 are independently hydrogen or methyl;

R3 is hydrogen; and n is zero, one or two.

2. The method of claim 1, wherein R1 and R2 are both hydrogen.

3. The method of claim 1, wherein $X_2$ is 4-fluoro.

4. The method of claim 1, wherein n is one.

5. The method of claim 1, wherein $X_1$ is a heteroaryl ring selected from the list consisting of 2-imidazolyl, 4-imidazolyl, 2-thiazolyl, 4-thiazolyl, 5-thiazolyl, 2-oxazolyl,4-oxazolyl, 5-oxazolyl, 1,2,4-thiadiazol-3-yl, 1,2,4-thiadiazol-2-yl, 1,2,4-thiadiazol-4-yl, 1,2,3-triazolyl-2-yl, 1,2,3-triazol-1-yl, 1,2,4-triazol-1-yl, 1,2,4-triazol-3-yl, 1,2,4-triazol-4-yl, 1,3-thiazol-2-yl, 1,3-thiazol-4-yl, 1,2,3,4-tetrazol-5-yl, 1,2,3,4-tetrazol-1-yl, 1,2,4-oxadiazol-3-yl, 1,2,4-oxadiazol-2-yl, 1,2,4-oxadiazol-3-yl, 1,2,4-oxadiazol-5-yl, 1,3-pyrimidin-2-yl, 1,2-pyrazin-3-yl and 1,2,4-triazin-3-yl.

6. The method of claim 1, wherein $X_1$ is a group of the general formula (II):

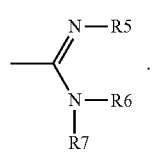

7. The method of claim 1, wherein R5 and R6, taken together with the N—C=N group to which they are attached form a 4-7 membered cyclic or bicyclic ring, wherein up to two carbon atoms are replaced with heteroatoms selected from the group consisting of N, O and S.

8. The method of claim 1, wherein R6 and R7, taken together with the nitrogen atom to which they are attached form a 4-7 membered cyclic or bicyclic ring, wherein up to two carbon atoms are replaced with heteroatoms selected from the group consisting of N, O and S or form a ring selected from azetidine, pyrrolidine, piperidine, azepine, piperazine, morpholine, thiomorpholine, oxazole and thiazole.

9. The method of claim 1, wherein R1 is hydrogen, R2 is hydrogen, R3 is hydrogen, n is one, $X_2$ is 4-fluoro.

10. The method of claim 1, wherein the compound is:
2-(1-[3-(dimethylamino)propyl]-1-(4-fluorophenyl)-1,3-dihydro-2-benzofuran-5-yl])-1H-imidazole.

11. The method of claim 1, wherein the compound is selected from the group consisting of:
2-(1-[3-aminopropyl]-1-(4-fluorophenyl)-1,3-dihydro-2-benzofuran-5-yl])-1H-imidazole;
2-(1-[3-(methylamino)propyl]-1-(4-fluorophenyl)-1,3-dihydro-2-benzofuran-5-yl])-1H-imidazole;
2-(1-[3-(dimethylamino)propyl]-1-(4-fluorophenyl)-1,3-dihydro-2-benzofuran-5-yl])-1,3-thiazole;
2-(1-[3-(dimethylamino)propyl]-1-(4-fluorophenyl)-1,3-dihydro-2-benzofuran-5-yl])-1,3-oxazole;
4-(1-[3-(dimethylamino)propyl]-1-(4-fluorophenyl)-1,3-dihydro-2-benzofuran-5-yl])-1,3-thiazole;
2-(1-[3-(dimethylamino)propyl]-1-(4-fluorophenyl)-1,3-dihydro-2-benzofuran-5-yl])-1,3-thiazole;
3-(1-[3-dimethylamino)propyl]-1-(4-fluorophenyl)-1,3-dihydro-2-benzofuran-5-yl])-1,2-isothiazole;
4-(1-[3-(dimethylamino)propyl]-1-(4-fluorophenyl)-1,3-dihydro-2-benzofuran-5-yl])-2-methyl-1H-imidazole;
5-(1-[3-(dimethylamino)propyl]-1-(4-fluorophenyl)-1,3-dihydro-2-benzofuran-5-yl])-2,4-dimethyl-1H-imidazole;
2-(1-[3-(dimethylamino)propyl]-1-(4-fluorophenyl)-1,3-dihydro-2-benzofuran-5-yl])-1H-1,3,4-triazole;
2-(1-[3-(dimethylamino)ethyl]-1-(4-fluorophenyl)-1,3-dihydro-2-benzofuran-5-yl])-1H-imidazole;
2-(1-[3-(dimethylamino)butyl]-1-(4-fluorophenyl)-1,3-dihydro-2-benzofuran-5-yl])-1H-imidazole;
2-(1-[3-(dimethylamino)propyl]-1-(4-fluorophenyl)-1,3-dihydro-2-benzofuran-5-yl])-4-methyl-1H-imidazole;
5-(1-[3-(dimethylamino)propyl]-1-(4-fluorophenyl)-1,3-dihydro-2-benzofuran-5-yl])-1H-tetrazole;
1-(1-[3-(dimethylamino)propyl]-1-(4-fluorophenyl)-1,3-dihydro-2-benzofuran-5-yl])-5-methyl-2H-tetrazole;
3-(1-[3-(dimethylamino)propyl]-1-(4-fluorophenyl)-1,3-dihydro-2-benzofuran-5-yl])-1,2,4-thiadiazole;
3-(1-[3-(dimethylamino)propyl]-1-(4-fluorophenyl)-1,3-dihydro-2-benzofuran-5-yl])-1,2,4-oxadiazole;
1-methyl-2-(1-[3-(dimethylamino)propyl]-1-(4-fluorophenyl)-1,3-dihydro-2-benzofuran-5-yl])-1H-imidazole;
4-methyl-2-(1-[3-(dimethylamino)propyl]-1-(4-fluorophenyl)-1,3-dihydro-2-benzofuran-5-yl])-1H-imidazole;
2(S)-2-(1-[3-(dimethylamino)propyl]-1-(4-fluorophenyl)-1,3-dihydro-2-benzofuran-5-yl])-1H-imidazole;
2(R)-2-(1-[3-(dimethylamino)propyl]-1-(4-fluorophenyl)-1,3-dihydro-2-benzofuran-5-yl])-1H-imidazole;
2-(1-[3-(dimethylamino)propyl]-1-(4-fluorophenyl)-1,3-dihydro-2-benzofuran-5-yl])-1H-benzimidazole;
4,5-dimethyl-2-(1-[3-(dimethylamino)propyl]-1-(4-fluorophenyl)-1,3-dihydro-2-benzofuran-5-yl])-1H-imidazole;
2-[1-[3-(dimethylamino)propyl]-1-(4-fluorophenyl)-1,3-dihydro-2-benzofuran-5-yl]-1,2,3,4-tetrahydro-1H-isoquinolin-2-yl)methanimine;
2-(1-[3-dimethylaminopropyl]-1-(4-fluorophenyl)-1,3-dihydro-2-benzofuran-5-yl})-1,3-pyrimidine;
3-(1[3-dimethylaminopropyl]-1-(4-fluorophenyl)-1,3-dihydro-2-benzofuran-5-yl})-1,2,4-triazine;
2-(1-[3-(dimethylamino)propyl]-1-(4-fluorophenyl)-1,3-dihydro-2-benzofuran-5-yl)-1H-4,5-dihydro-imidazole;
2-(1-[3-(dimethylamino)propyl]-1-(4-fluorophenyl)-1,3-dihydro-2-benzofuran-5-yl)-4,5,6,7-tetrahydro-1H-1,3-diazepine; and
2-(1-[3-(dimethylamino)propyl]-1-(4-fluorophenyl)-1,3-dihydro-2-benzofuran-5-yl)-1,4,5,6-tetrahydro-pyrimidine.

12. The method of claim 1, wherein the mammal is a human.

* * * * *